United States Patent [19]
Beachy et al.

[11] Patent Number: 5,824,857
[45] Date of Patent: Oct. 20, 1998

[54] PLANT PROMOTER

[75] Inventors: Roger N. Beachy, LaJolla, Calif.; Maitrayee Bhattacharyya, St. Louis, Mo.

[73] Assignee: Washington University, St. Louis, Mo.

[21] Appl. No.: 789,738

[22] Filed: Nov. 8, 1991

[51] Int. Cl.[6] ............................ C12N 15/82; C12N 15/05
[52] U.S. Cl. ........................ 800/205; 800/235; 435/410; 435/419; 536/23.4; 536/23.6; 536/24.1
[58] Field of Search .................. 530/27; 435/240.44, 435/172.3, 320.1, 410, 419; 800/205, DIG. 55, DIG. 57, 235; 935/6, 30, 67; 536/24.1

[56] References Cited

PUBLICATIONS de Kochko et al; J. Cell. Biochem. Suppl. 15A, p. 146 (1991).

"An auxin–sensitive promoter and a rice tungro virus promoter driving the gusA gene in transgenic rice plants" from the Fifth Annual Meeting of the Rockefeller Foundation on Rice Biotechnology which tool place in Tuscon, Arizona on Oct. 2–5, 1991 written by Jianying Peng, Halina Kononowicz, Fujiang Wen and Thomas K. Hodges.

"Indica Rice Regeneration and Transformation" from the Progress Report—Rockefeller Foundation Annual Meeting in Tuscon, Arizona, Oct. 1991 written by Thomas K. Hodges, J–Y, Peng, R–C Su, F. Wen, H. Kononowicz, D. Koetje, X–Q. Li, and M. Rudert.

Primary Examiner—James Martinell
Attorney, Agent, or Firm—Howell & Haferkamp, L.C.

[57] ABSTRACT

A genome length transcript promoter from a badnavirus, rice tungro bacilliform virus (RTBV), is disclosed and its DNA sequence provided. This promoter drives expression specifically in vascular tissues of plants. This promoter sequence may be utilized in a chimeric gene to drive the tissue specific expression of a foreign structural gene in vascular tissue of transgenic plants.

24 Claims, 4 Drawing Sheets

DNA Sequence of promoter fragment pMB9089

AGATCTTCTA.CAAAAGGGAG.TAGTAATATT.TAATGAGCTT.GAAGGAGGAT.ATCAACTCTC.
TCCAAGGTTT.ATTGGAGACC.TTTATGCTCA.TGGTTTTATT.AAACAAATAA.ACTTCACAAC.
CAAGGTTCCT.GAAGGGCTAC.CGCCAATCAT.AGCGGAAAAA.CTTCAAGACT.ATAAGTTCCC.
TGGATCAAAT.ACCGTCTTAA.TAGAACGAGA.GATTCCTCGC.TGGAACTTCA.ATGAAATGAA.
AAGAGAAACA.CAGATGAGGA.CCAACTTATA.TATCTTCAAG.AATTATCGCT.GTTTCTATGG.
CTATTCACCA.TTAAGGCCAT.ACGAACCTAT.AACTCCTGAA.GAATTTGGGT.TTGATTACTA.
CAGTTGGGAA.AATATGGTTG.ATGAAGACGA.AGGAGAAGTT.GTATACATCT.CCAAGTATAC.
TAAGATTATC.AAAGTCACTA.AAGAGCATGC.ATGGGCTTGG.CCAGAACATG.ATGGAGACAC.
AATGTCCTGC.ACCACATCAA.TAGAAGATGA.ATGGATCCAT.CGTATGGACA.ATGCTTAAAG.
AAGCTTTATC.AAAAGCAACT.TTAAGTACGA.ATCAATAAAG.AAGGACCAGA.AGATATAAAG.
CTGGAACATC.TTCACATGCT.ACCACATGGC.TAGCATCTTT.ACTTTAGCAT.CTCTATTATT.
GTAAGAGTGT.ATAATGACCA.GTGTGCCCCT.GGACTCCAGT.ATATAAGGAG.CACC

Figure 1

DNA Sequence of promoter fragment pMB1709

AGATCTTCTA.CAAAAGGGAG.TAGTAATATT.TAATGAGCTT.GAAGGAGGAT.ATCAACTCTC.
TCCAAGGTTT.ATTGGAGACC.TTTATGCTCA.TGGTTTTATT.AAACAAATAA.ACTTCACAAC.
CAAGGTTCCT.GAAGGGCTAC.CGCCAATCAT.AGCGGAAAAA.CTTCAAGACT.ATAAGTTCCC.
TGGATCAAAT.ACCGTCTTAA.TAGAACGAGA.GATTCCTCGC.TGGAACTTCA.ATGAAATGAA.
AAGAGAAACA.CAGATGAGGA.CCAACTTATA.TATCTTCAAG.AATTATCGCT.GTTTCTATGG.
CTATTCACCA.TTAAGGCCAT.ACGAACCTAT.AACTCCTGAA.GAATTTGGGT.TTGATTACTA.
CAGTTGGGAA.AATATGGTTG.ATGAAGACGA.AGGAGAAGTT.GTATACATCT.CCAAGTATAC.
TAAGATTATC.AAAGTCACTA.AAGAGCATGC.ATGGGCTTGG.CCAGAACATG.ATGGAGACAC.
AATGTCCTGC.ACCACATCAA.TAGAAGATGA.ATGGATCCAT.CGTATGGACA.ATGCTTAAAG.
AAGCTTTATC.AAAAGCAACT.TTAAGTACGA.ATCAATAAAG.AAGGACCAGA.AGATATAAAG.
CTGGAACATC.TTCACATGCT.ACCACATGGC.TAGCATCTTT.ACTTTAGCAT.CTCTATTATT.
GTAAGAGTGT.ATAATGACCA.GTGTGCCCCT.GGACTCCAGT.ATATAAGGAG.CACCAGAGTA.
GTGTAATAGA.TCATCGATCA.AGCAAGCGAG.AGCTCAAACT.TCTAAGAGAG.CAA

PLANT PROMOTER

FIELD OF THE INVENTION

This invention relates to the expression of a foreign gene in a plant, and more particularly to a DNA promoter sequence capable of driving expression of a gene in specific tissues of a plant.

BACKGROUND OF THE INVENTION

It is a primary goal of research efforts in plant biotechnology to utilize recombinant DNA technology to genetically engineer plant species so that they have a new or improved trait or characteristic. In recent years, scientists have applied this technology successfully to many different plant species and transgenic plants having new or improved traits or characteristics have been produced.

A desired trait or characteristic is introduced into the plant by the introduction into the genome of the plant a gene that encodes for the polypeptide that confers the desired trait or characteristic. In order for the introduced gene to be expressed in the plant, DNA sequences that regulate the expression of the gene must also be introduced into the plant in conjunction with the desired gene. For expression of a gene in a plant, the necessary regulatory sequences include a promoter (which may include a leader sequence, but a leader sequence may be included separately from the promoter), and a 3' non-translated region that functions in plant cells to cause the addition of polyadenylated nucleotides to the 3' end of the transcribed messenger RNA (mRNA) sequence.

The promoter sequence is an integral part of any DNA inserted into plant cells because it is the sequence of DNA that controls and regulates the transcription of the gene associated with the promoter which results in the production of mRNA. In plants, RNA polymerase II interacts with the promoter to initiate transcription of the gene and, ultimately, the production of a strand of mRNA which, in turn, is translated into the polypeptide encoded by the gene.

Scientists in the field of plant biotechnology have identified a number of promoters that are capable of causing gene expression in plants. One of the most widely used promoters in this field is the full-length transcript promoter from Cauliflower mosaic virus (CaMV35S). The cauliflower mosaic virus (CaMV) is a member of the caulimovirus group and is identified by its circular double-stranded DNA genome. Chimeric genes under the transcriptional control of the CaMV35S promoter exhibit a strong and constitutive pattern of expression in both dicotyledonous and monocotyledonous transgenic plants. The CaMV35S promoter has become the preferred promoter in plant biotechnology and is widely used to cause the expression of a variety of different genes in many different plant species. The full-length transcript promoter from another member of the caulimovirus group, the figwort mosaic virus, was identified recently. This promoter also displays a strong and constitutive pattern of expression in transgenic plants, similar to that of the CaMV35S promoter, although there is evidence that it provides even stronger constitutive expression than the CaMV35S promoter in plants.

Even though providing constitutive expression of a gene in plants is often desirable, it is also desirable in some instances to direct expression of a gene to particular tissues in a plant. Some tissue specific plant promoters are known, such as those capable of directing expression preferentially in the fruit of a plant, but the genome length transcript, i.e. full length transcript or major transcript, promoters that have been obtained from double-stranded DNA plant viruses all display strong, constitutive expression patterns. Extensive structure analysis of the CaMV35S promoter sequence has identified domains within the viral promoter sequence that confer tissue specificity (Odell et al. 1985; Benfey et al. 1989; Fang et al. 1989), but the promoter sequence in its entirety is a constitutive promoter.

A second group of plant viruses that possess a double-stranded DNA genome have been described (Lockhart 1990). These viruses are morphologically bacilliform and are called badnaviruses. The rice tungro bacilliform virus (RTBV) is a member of the badnavirus group and is a pathogen to some monocotyledonous plants, including rice. Heretofore, the nature of the expression characteristics of the genome length transcript promoter from badnaviruses such as RTBV were unknown.

SUMMARY OF THE INVENTION

It has been discovered that the genome length transcript promoter from the rice tungro bacilliform virus unexpectedly exhibits a tissue specific expression pattern of a structural gene under the regulatory control of the promoter. The RTBV promoter causes preferential expression in plant vascular tissue. A transgenic plant expressing a foreign structural gene under the control of the RTBV genome length transcript promoter expresses the polypeptide encoded by the gene specifically in the vascular tissues of the plant. The isolated DNA sequence of the genome length promoter comprises at least the 684 base pairs (bp) upstream of the transcription start site of the RTBV genomic sequence. Two promoter fragments from RTBV, one 714 bp in length and another 773 bp in length, were isolated and used to drive expression of a foreign gene in monocotyledonous and dicotyledonous plant tissue.

Other aspects of the invention include a chimeric gene that functions in plant cells which is comprised of the genome length transcript promoter from RTBV, a structural DNA sequence heterologous to the promoter and a 3' non-translated polyadenylation region; a transformed plant cell comprising this chimeric gene; and transgenic plants comprising a gene regulated by a genome length transcript promoter from RTBV, where the gene is heterologous to the promoter. The invention further comprises a method for making a transgenic plant by introducing a chimeric gene into plant cells where the chimeric gene is comprised of a genome length transcript promoter from RTBV, a structural gene that is heterologous with respect to the promoter, and a 3' non-translated polyadenylation region, culturing the plant cells in a culturing medium containing a selection agent to identify transformed plant cells and regenerating the plant cells into whole plants. Also described is a method for expressing a foreign structural gene in a plant under the regulatory control of a genome length transcript promoter from RTBV.

BRIEF DESCRIPTION OF THE DRAWINGS

FIG. 1 illustrates a 714 base pair nucleotide sequence containing the genome length transcript promoter from RTBV.

FIG. 2 illustrates a 773 base pair nucleotide sequence containing the genome length transcript promoter from RTBV.

FIG. 3 is a schematic representation of the preparation of transformation vectors containing a RTBV promoter sequence.

DETAILED DESCRIPTION OF THE PREFERRED EMBODIMENTS

Figure 4:
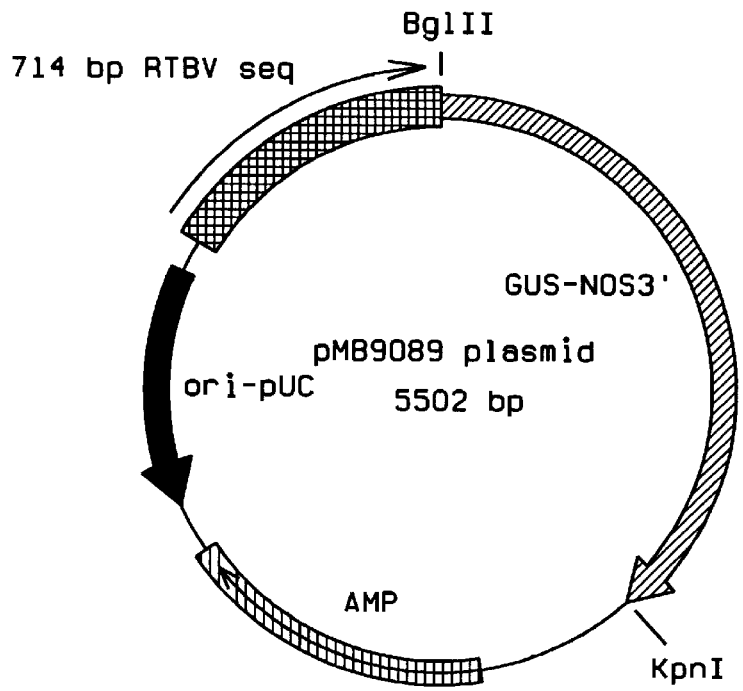
FIG. 4 is a physical map of pMB9089.

The plant promoter according to the present invention comprises a genome length transcript promoter from the rice tungro bacilliform virus. As used in the following specification, the phrase "genome length transcript promoter" or "major transcript promoter" means the promoter region of a viral genome that is responsible for transcription of the genome length RNA from the viral genome. The genome length transcript promoter from RTBV of the present invention exhibits a specificity for expression of a structural gene under its regulatory control in vascular tissues of a plant.

The complete nucleotide sequence and genome organization of a full-length clone of the RTBV genome has been reported in Qu et al. (1991) Virology 185, 354–364. From this information, the transcription start site was identified and the putative promoter region of the RTBV genome was also identified. In order to determine whether this promoter region was capable of driving the expression of a foreign, heterologous gene in a plant, the putative promoter region was isolated and tested for the existence of promoter activity.

Two RTBV genome length transcript promoter fragments were synthesized utilizing the PCR technology. Oligonucleotide primers containing terminal BglII sites and corresponding to particular DNA segments of the RTBV genome near the putative promoter region were used. Intact RTBV genomic DNA was used as the template for synthesis of the promoter fragments. The RTBV genomic DNA used as the template was extracted from RTBV virions provided by Dr. H. Hibino of the International Rice Research Institute (Los Banos, Philippines) as described in Jones et al. (1991).

One RTBV promoter sequence was synthesized from the RTBV genomic DNA by PCR using an oligonucleotide primer having the nucleotide sequence:

5'-AGAAGATCTTCTACAA-3'  (SEQ ID NO: 1)

which is the RTBV genomic nucleotide sequence corresponding to nucleotides 6671 to 6686 as numbered in Qu et al. (1991), and an oligonucleotide primer having the nucleotide sequence:

5'-AGATCTGGTGCTCCTTAT-3'  (SEQ ID NO: 2)

which is complementary to the RTBV genomic sequence from nucleotides 7389 to 7373. The promoter fragment is cut with BglII such that the nucleotide sequence inserted into the expression plasmid contains nucleotides 6675–7389. The resulting PCR synthesized RTBV genome length transcript promoter contains 714 bases of the RTBV genome including the entire promoter sequence. The transcription start site for the terminally redundant RTBV transcript lies 32 bases from the 3' terminus of this PCR fragment. The nucleotide sequence of this promoter fragment from RTBV is shown in FIG. 1 and is identified as SEQ ID NO: 3.

The second RTBV promoter sequence isolated has 773 nucleotides of RTBV sequence. This promoter fragment was synthesized by using SEQ ID NO: 1 as one oligonucleotide primer and an oligonucleotide primer having the following sequence:

5'-AGATCTTGCTCTCTTAGAAGTTT-3'  (SEQ ID NO: 4)

which is complementary to the RTBV sequence from nucleotides 7446 to 7431. The resulting PCR synthesized RTBV genome length transcript promoter includes the entire RTBV promoter region. The endogenous RTBV transcription start site is 92 nucleotides upstream of the 3' terminus of this promoter fragment. The nucleotide sequence of this promoter fragment is shown in FIG. 2 and is identified as SEQ ID NO: 5. Each of these synthesized RTBV genome length transcript promoter regions contain all of the 684 nucleotides upstream of the transcription start site of the RTBV transcript. The transcription start site has been identified at nucleotide 7354 of the RTBV genome. The 684 bp promoter sequence extends from nucleotides 6670–7354 of the RTBV genome.

Figure 3:
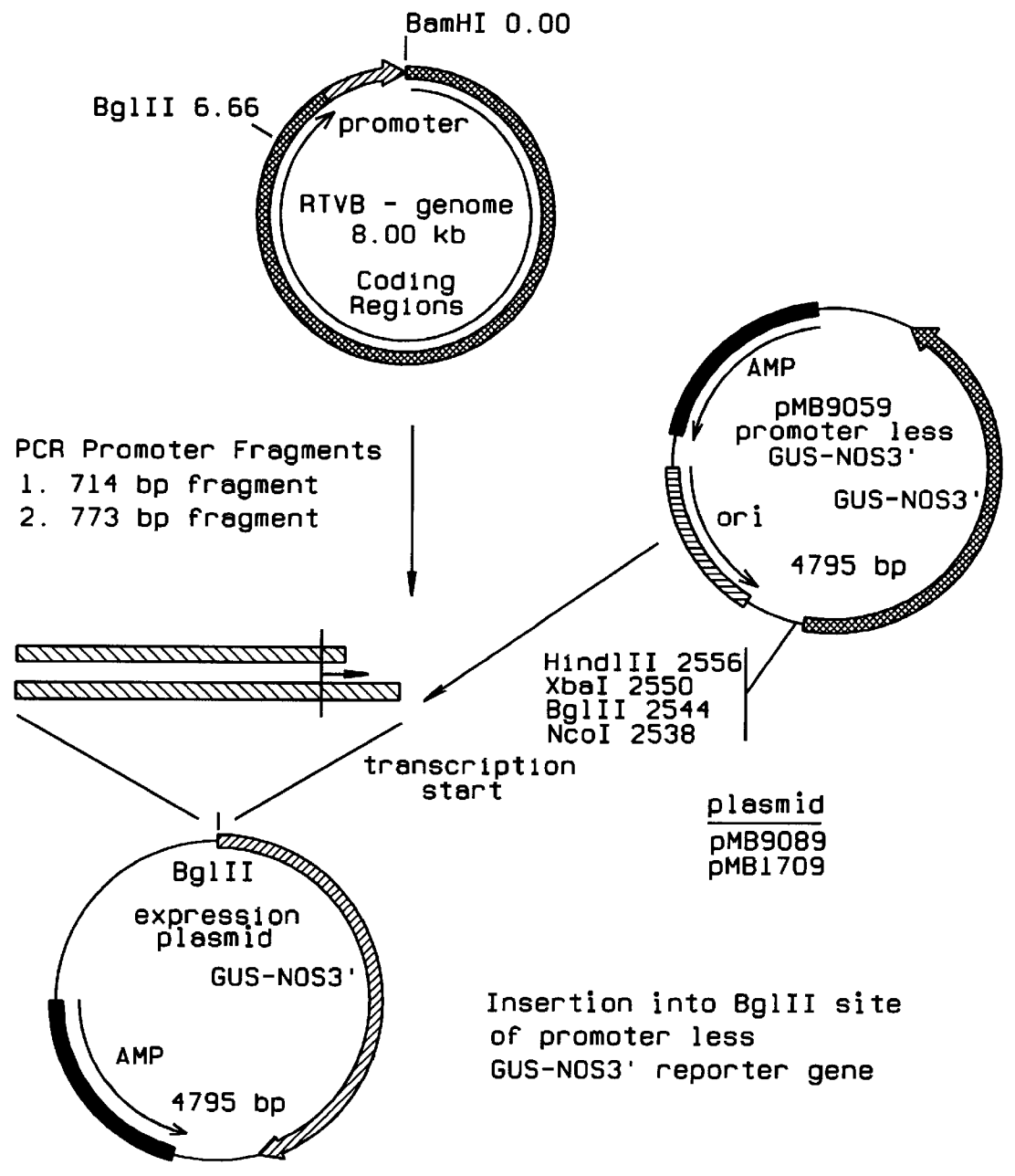
Figure 5:
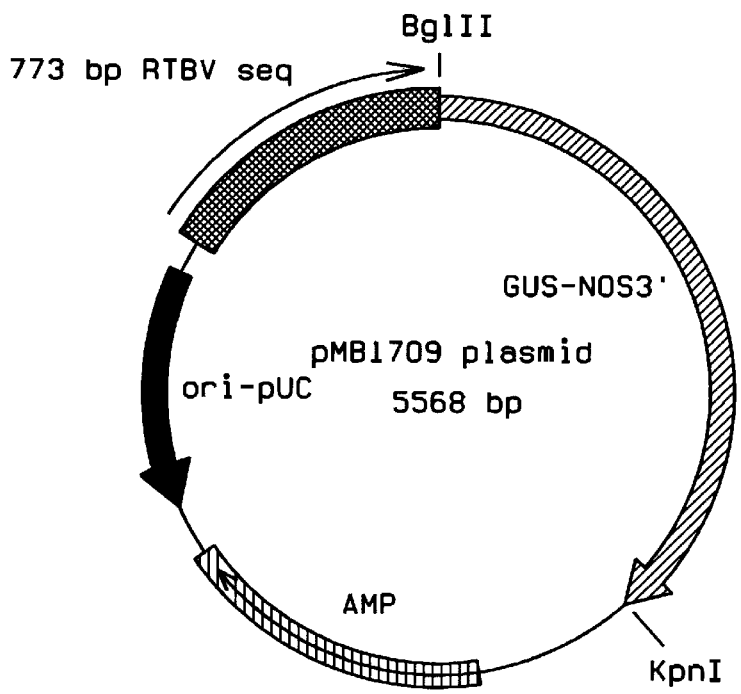
FIG. 5 is a physical map of pMB1709.

Each of these RTBV promoter sequences was inserted into plant transformation vectors to determine the promoter activity of the fragments. FIG. 3 schematically illustrates the preparation of the transformation vectors used for this determination. After being treated with BglII endonuclease, the RTBV promoter sequences were inserted into the unique BglII site of pMON9059 which has a "promoter-less" GUS-NOS 3' reporter gene. The GUS gene encodes for the bacterial β-glucuronidase. Insertion of the 714 bp RTBV promoter region synthesized by PCR resulted in pMB9089 which is illustrated in FIG. 4 and insertion of the 773 bp RTBV promoter region synthesized by PCR resulted in pMB1709 which is illustrated in FIG. 5.

As described more fully in the Examples to follow, plant cells transformed with either pMB9089 or pMB1709 exhibited promoter activity by the appearance of blue spots indicating expression of the GUS gene in transformed protoplasts from rice, tobacco and maize when assayed for β-glucuronidase activity. When the RTBV genome length transcript promoter containing plasmids were introduced into intact leaf tissue of rice, promoter activity was again confirmed by the appearance of blue spots in the leaf tissue when assayed for β-glucuronidase activity. Surprisingly, analysis of the expression pattern of the GUS spots in transient assays of rice leaf tissue transformed with the RTBV genome length transcript promoter revealed the preferential specificity of the RTBV promoter for the vascular tissue of the transformed leaf tissue.

While the RTBV isolate and promoter fragments described above were used to illustrate the promoter of the present invention, other RTBV isolates could be used as the source of the genome length transcript promoter and other methods of obtaining the promoter could be employed. The use of the described RTBV genome as the source of the promoter regions of the present invention was for illustrative purposes only. Other isolates of RTBV are known and by following techniques similar to those described herein or those known in the art, one could obtain a genome length transcript promoter from other RTBV isolates. Other isolates of RTBV are known to have been isolated from India, Southeast Asia and Asia. To determine whether other RTBV promoters isolated from a different isolate have characteristics similar to those described herein, one would examine the expression pattern of the so isolated RTBV genome length transcript promoter using techniques as described herein. Those skilled in the art also know that techniques other than PCR could be used to obtain the genome length transcript promoter from an RTBV genome. The genome length transcript promoter could, alternatively, be isolated directly from the RTBV genome or from a clone of RTBV DNA.

Once isolated, a DNA sequence comprising the genome length transcript promoter from RTBV can be used in a chimeric gene construct to cause the tissue specific expression of a foreign or heterologous structural gene regulated by the promoter. As used in this specification, the term "foreign" or "heterologous" structural gene means that the structural gene does not naturally occur in association with the promoter described. The term "structural gene" means DNA coding region. Using known, routine DNA manipulation techniques such as those described in Sambrook et al. (1989), chimeric genes can be constructed whereby a desired foreign structural DNA sequence, or gene, can be placed under the regulatory control of a genome length transcript promoter from RTBV. For expression in plants, the chimeric gene will also contain a 3' non-translated region that functions in plant cells to cause the addition of polyadenylated nucleotides to the 3' end of the transcribed RNA sequence (the 3' non-translated region). Examples of suitable 3' non-translated polyadenylation regions are the 3' polyadenylation region from the nopaline synthase gene (NOS) of the Ti plasmid from *Agrobacterium tumefaciens* and the 3' non-translated region from the pea E9 small subunit of the ribulose bisphosphate carboxylase gene (ssRUBISCO).

Any desired structural gene may be placed under the regulatory control of the RTBV genome length transcript promoter. The structural gene may encode for any desired polypeptide or other gene product. In plant species which are of major agronomic importance, such as the legumes and cereal crops, the structural gene preferably encodes for a polypeptide which confers a desired agronomic trait or characteristic to the plant. Examples of desirable agronomic traits are too numerous to list, but include drought tolerance, herbicide tolerance, insect tolerance and viral tolerance.

Once a chimeric gene containing a foreign gene under the regulatory control of the RTBV genome length transcript promoter and a 3' non-translated region is prepared, the chimeric gene can be introduced into an appropriate plant transformation vector, and plant transformation of the desired plant species carried out using known techniques. Chimeric genes containing the promoter of the present invention can be inserted into the genome of a plant by standard techniques. If Agrobacterium mediated delivery is chosen as the transformation method, transformation vectors such as those disclosed by Herrera-Estrella (1983), Bevan (1983), Klee (1985) and U.S. Pat. No. 4,940,838 are suitable. Alternative methods of transformation such as electroporation, and the microprojectile bombardment method of DNA delivery are also suitable for use with the chimeric genes of this invention.

The construction of vectors suitable for any of these transformation techniques is known and routine to those of ordinary skill in the art. Generally, for Agrobacterium mediated delivery, the transformation vector will include selectable and scoreable marker genes, T-DNA borders, cloning sites, appropriate bacterial genes to facilitate identification of transconjugates, broad host range replication and mobilization functions, and other elements as desired. When electroporation or microprojectile bombardment transformation techniques are utilized, the transformation vector generally contains the desired chimeric gene and a selectable marker gene construct to determine whether the transformation event was successful.

Transformed plant cells are obtained as a result of the transformation of the plant cells with a chimeric gene construct containing the RTBV genome length transcript promoter and the desired foreign gene. These plant cells are then cultured in a culturing medium containing the appropriate selection agent to identify and select for plant cells containing the chimeric gene. After plant cells that contain the desired chimeric gene are identified, whole plants are regenerated from these plant cells. Techniques for regenerating whole plants from transformed plant cells are known in the art for most of the major plant species. Suitable plant regeneration protocols are known for many of the dicotyledonous plants and most of the major monocotyledonous plants.

The RTBV promoter of this invention can be used to drive expression specifically in the vascular tissue of most plant species, monocotyledonous or dicotyledonous. The promoter exhibits stronger expression in monocotyledonous plants and is particularly suited for use in rice.

Generally, preparation of plasmid DNA, chimeric genes, restriction endonucleases digestion, transformation and confirmation of transformation by selection are carried out using standard techniques (Sambrook et al. 1989).

The following examples are provided to illustrate the promoter of the present invention and should not be interpreted in any way to limit the scope of the invention. Those skilled in the art will recognize that various modifications can be made to the procedures described herein without departing from the spirit and scope of the present invention.

EXAMPLE 1

Protoplasts from a *Zea maize* var. Black Mexican Sweet cell suspension culture (BMS-EG5) provided by C. L. Armstrong of Monsanto Co. (St. Louis, Mo.) were prepared and transformed with DNA constructs to determine the promoter activity of the isolated RTBV genome length transcript promoter fragments. This BMS-EG5 cell line was selected for high protoplast plating efficiency through repeated cycles of protoplast culture and selection. This cell line is not embryogenic. The cultures were maintained by weekly subculturing of 5 mls of suspended cells into 35 mls MSEG5 medium consisting of MS salts with supplements (Armstrong et al. 1990). Cells were grown in 250 ml Erlenmeyer flasks at 120 rpms, 28° C., in the dark. Cells were collected at two days post-subculture for protoplast isolation. One gram fresh weight of cells was treated with 10 mls of an enzyme solution consisting of 2% cellulase (CEL; Worthington Biochemical Corp.) and 0.1% Pectolyase Y23 (Seishin Pharmaceutical Co. Ltd), dissolved in 0.2M mannitol and 80 mM $CaCl_2$ (MaCa), and adjusted to a final pH of 4.3. Cells were digested with slow agitation (~50 rpm, using 10–20 mls enzyme solution in a 100×25 mm petri dish) for 1.5 hours, in the dark, at 28° C. Protoplasts were collected by centrifugation at 100×g, washed twice in MaCa, diluted and samples counted with a hemocytometer. Protoplast yields ranged from 8 to 16 million protoplasts per gram fresh weight of cells.

These maize protoplasts were electroporated with either pMB9089 or pMB1709 as previously described by the following procedure. A capacitor discharge system was used to deliver a 150V pulse at a capacitance of 500 $\mu$F. Protoplasts were electroporated at a density of $2.5\times10^6$ cells/ml in electroporation medium, with mannitol as osmoticum, pH 7.2 (Fromm et al. 1987). Pulses were delivered into 800 $\mu$l of protoplast suspension in an electroporation cuvette (BioRad) with the electrodes 0.4 cm apart. Two samples were electroporated for each DNA construct. The electroporated samples were incubated on ice for 10 minutes, room temperature for 10 minutes and finally plated after dilution with 15 mls of conditioned medium. Following electroporation, protoplasts were resuspended at 400,000 per ml in filter sterilized 100% conditioned medium (CM)

containing 8% mannitol. The "conditioned medium" was spent medium in which the cells had been growing. Protoplasts were then incubated at 26° C. in the dark for either 24 or 48 hours. After culturing, the number of surviving protoplasts were counted in ten random fields using a Zeiss microscope. Dead protoplasts were clearly distinguished by granular cytoplasm; the viability was also confirmed by staining with fluorescein diacetate (Widholm 1972). Following incubation the cells were harvested by centrifugation and resuspended in extraction buffer.

The protoplasts were stored in extraction buffer at −80° C. GUS activity was determined after grinding thawed protoplasts using a tissue grinder. The extracts were centrifuged at high speed in a clinical centrifuge for 5 minutes and the supernatant removed for use in GUS assays. The GUS assay was performed, and GUS activity measured, according to Jefferson et al. (1987) using 50 μl of extract and X-gluc as the substrate.

In maize protoplasts, GUS activity was positive for protoplasts electroporated with either RTBV genome length transcript promoter containing construct which confirmed the promoter activity of the isolated RTBV DNA regions. As a control, maize protoplasts were also electroporated by the same procedure with a vector containing a GUS gene under the regulatory control of the enhanced CaMV35S promoter (Kay et al. 1987). The levels of GUS expression in maize protoplasts was low when compared to the protoplasts transformed with the control construct and protoplasts transformed with the pMB1709 construct containing the 773 bp RTBV promoter were not significantly above background levels.

EXAMPLE 2

Rice protoplasts were also electroporated with either the pMB9089 or pMB1709 constructs to test the activity of the RTBV promoter fragments in rice.

A rice cell suspension culture was derived from *Oryzae sativa* cultivar IR54, provided by T. Hodges, Purdue University. The suspension culture was maintained by weekly subculture in N6 medium (Chu et al. 1975). Prior to generation of protoplasts, the cells were subcultured into MS medium (Peng et al. 1990). Rice cells were grown in the dark as described for the maize BMS cells in Example 1. Cells were collected two days post-subculture into MS medium for protoplast isolation. Cells were digested in an enzyme solution consisting of 2% cellulase, 3.0% Macerozyme R-10 and 0.5% Pectolyase Y23, in 0.4M glucose and 5 mM MES, adjusted to a final pH of 5.8. Cells were digested with slow agitation (~50 rpm, using 10–20 mls enzyme solution in a 100×25 mm petri dish) for approximately 6 hours, in the dark, at 28° C. Protoplasts were collected by centrifugation at 100×g, washed twice in MaCa adjusted to a final pH of 5.8 and samples counted with a hemocytometer.

The rice protoplasts were electroporated with either pMB9089 or pMB1709 as described in Example 1 and the GUS activity assays were as previously described.

In transient GUS assays, both DNA constructs containing either the 714 or the 773 bp RTBV promoter fragment exhibited low, but significant GUS activity in protoplasts when compared with the level of GUS expression obtained from the control construct, which was as described in Example 1. Again, the rice protoplasts transformed with the 714 bp RTBV genome length transcript promoter fragment exhibited higher levels of expression than protoplasts transformed with the 773 bp RTBV promoter fragment in pMB1709. This example confirmed the promoter activity and ability of the RTBV genome length transcript promoter to drive expression of a foreign gene under its transriptional control.

EXAMPLE 3

Protoplasts were also prepared from a tobacco suspension culture provided by D. Deboer (Monsanto Co., St. Louis, Mo.). This cell line was selected for rapid growth through repeated cycles of protoplast subculture and is not embryogenic. The cultures were maintained by subculturing every three days by transferring 15 mls of suspended cells into 25 mls of fresh TXD medium. Cells were grown in 250 ml Erlenmeyer flasks at 120 rpms, 28° C., in the dark. Cells were collected 24 hours post-subculture for protoplast isolation and digested in an enzyme solution consisting of 2% cellulase and 0.1% Pectolyase Y23 dissolved in MaCa and adjusted to a final pH of 5.8. Cells were digested with slow agitation (~50 rpm) using 10–20 mls enzyme solution in a 100×25 mm petri dish for 1.5 hours in the dark at 28° C. Protoplasts were collected by centrifugation at 100×g, washed twice in MaCa and samples counted with a hemocytometer.

These tobacco protoplasts were electroporated with either of the RTBV genome length transcript promoter containing constructs, pMB9089 or pMB1709, as described in Example 1. The GUS assays and measurement were also as described in Example 1.

In tobacco protoplasts, the RTBV promoters were active, but at very low levels. The constructs containing the 714 bp RTBV promoter fragment again exhibited stronger levels of expression than the constructs containing the 773 bp RTBV promoter fragment. Each construct containing the genome length transcript promoter from RTBV also again exhibited lower levels of expression than the control construct.

EXAMPLE 4

Fresh leaf tissue from rice was also transformed with the DNA constructs previously described to determine the promoter activity and expression characteristics of the isolated RTBV promoter fragments in intact tissue. After a brief surface sterilization, etiolated leaf tissue from three week old rice plants was isolated by removing the green portions of the leaf base to expose younger, non-green tissue.

This leaf tissue was transformed by the microprojectile bombardment technique using M10 tungsten particles prepared for use as described in Franche et al. (1991). The particles contained either PMB9089 or pMB1709 and were finally resuspended in 0.5 ml sterile 50% glycerol after the final water rinse.

The particles were sonicated briefly to disperse particles thoroughly immediately before beginning the DNA precipitation. A 12.5 μl aliquot of particles were combined with 2.5 μg of the DNA construct of interest, and 17.5 μl of freshly prepared 1.0M $CaCl_2$ and 0.1M spermidine in a ratio of 5:2 were added to the particles and mixed quickly. The particles were incubated at room temperature for 10 minutes and 12.5 μl of supernatant removed. The mixture was sonicated briefly to resuspend the particles prior to bombardment. Two and one-half μl of particles with bound DNA were used per bombardment. Any suitable microprojectile accelerating device can be used to introduce the particles into the intact leaf tissue. The Biolistics PDS 1000 was used for these experiments.

Subsequent to bombardment, the leaf tissue was assayed for the appearance of blue spots indicating successful transformation and expression of the GUS gene under the control of the RTBV genome length transcript promoter as described in Example 1.

Expression from the chimeric gene constructs containing the RTBV genome length transcript promoter fragments in rice leaf tissue was again quantitatively lower than the levels of expression of the control construct, however, the transient GUS assays of the rice leaf tissue for the expression of the GUS gene displayed a specificity for expression of the GUS gene in the vascular tissue of the transformed leaf tissue. The observed blue spots evidencing GUS expression were located primarily on the vascular tissue of the transformed rice leaf. These results illustrate the tissue specific nature and preference for expression in vascular tissue of the RTBV genome length transcript promoter. This tissue specific expression pattern was exhibited by both the 714 and the 773 bp RTBV promoter fragment containing constructs. The regeneration of whole transformed rice plants from these transformed cells will also exhibit this tissue specific expression pattern in the vascular tissues of the whole plant.

BIBLIOGRAPHY

Armstrong C. A. et al. (1990), Plant Cell Rep. 9: 335–339.
Benfey, P. N., Ren, L., and Chua, N.-H. (1989), EMBO J. 8, 2195–2202.
Bevan, M., et al., Nature, 304: 184 (1983).
Chu, C. C., Wang, C. C., Hsu, C., Yin, K. C., Chu, C. Y., and bin, F. Y., (1975), Scientia Sinica, Vol. 18: 659–668.
Fang, R.-X., Nagy, F., Sivasubraminiam, S., Chua, N.-H., (1989), The Plant Cell, Vol. 1: 141–150.
Franche-Bogusz, C., et al., (1991), Plant Cell Reports, in press.
Fromm, M., Callis, J., Taylor, L. P., Walbot, V., (1987), Methods in Enzymology, Vol. 153: 351–366.
Herrera-Estrella, L., et al., Nature, 3093: 209 (1983).
Jefferson, R. A., (1987), Plant Molecular Biology Reporter, Vol. 5: 387–405.
Jones, M., Gough, K., Dasgupta, I., Subba Rao, B. L., Cliffe, J., Qu, R., Shen, P., Kaniewska, M. B., Davies, J. B., Beachy, R. N., Hull, R., (1991), Journal of General Virology, Vol. 72: 757–761.
Kay, R., Chan, A., Daly, M. and McPherson, J., (1987), Science 236: 1299–1302.
Klee, H., et al., Bio/Technology, 3: 637 (1985).
Lockhart, B. E. L., (1990), Phytopathology, Vol. 80: 127–131.
Odell, J. T., F. Nagy and N.H. Chua (1985), Nature 313: 810–812.
Peng, J., Lyanik, L. A., Lee, L. and Hodges T. K. 1990, Plant Cell Reports 9: 168–172.
Sambrook, J., Fritsch, E. F., and maniatis, T. (1989), Cold Spring Harbor Laboratory, Cold Spring Harbor, N.Y.
Widholm, J., (1972), Stain Technology, Vol. 47: 189–194.

What is claimed is:

1. An isolated genome-length transcript promoter from rice tungro bacilliform virus.

2. A promoter of claim 1 having the nucleotide sequence of SEQ ID NO: 3.

3. A promoter of claim 1 having the nucleotide sequence of SEQ ID NO: 5.

4. A chimeric gene that functions in plant cells comprising:
   a genome-length transcript promoter from rice tungro bacilliform virus;
   a structural DNA sequence that is heterologous with respect to said promoter; and
   a 3' non-translated DNA sequence which functions in plants to cause the addition of polyadenylated nucleotides to the 3' end of the transcribed sequence.

5. A chimeric gene of claim 4 wherein said promoter is SEQ ID NO: 3.

6. A chimeric gene of claim 4 wherein said promoter is SEQ ID NO: 5.

7. A chimeric gene of claim 4 wherein said structural DNA sequence encodes a protein capable of conferring a selected agronomic trait to a plant.

8. An isolated genome-length transcript promoter from rice tungro bacilliform virus capable of driving transcription of a structural DNA sequence operably coupled thereto in the vascular bundles of a plant.

9. A transformed plant cell comprising a chimeric gene comprised of:
   a genome-length transcript promoter from rice tungro bacilliform virus;
   a structural DNA sequence that is heterologous with respect to said promoter; and
   a 3' non-translated DNA sequence which functions in plants to cause the addition of polyadenylated nucleotides to the 3' end of the transcribed sequence.

10. A transformed plant cell of claim 9 wherein said promoter is SEQ ID NO: 3.

11. A transformed plant cell of claim 9 wherein said promoter is SEQ ID NO: 5.

12. A transgenic plant comprising a gene regulated by a genome-length transcript promoter from rice tungro bacilliform virus, wherein said gene is heterologous with respect to said promoter.

13. A transgenic plant of claim 12 wherein said gene is capable of conferring a selected agronomic trait to said plant.

14. A transgenic plant of claim 12 wherein said plant is a species of plant from the Graminae family.

15. A transgenic plant of claim 14 wherein said plant is rice.

16. A method of making a transgenic plant comprising:
   introducing a chimeric gene into plant cells of a plant, said chimeric gene comprised of a genome-length transcript promoter from rice tungro bacilliform virus, a structural DNA sequence that is heterologous with respect to said promoter, and a 3' non-translated DNA sequence which functions in plants to cause the addition of polyadenylated nucleotide to the 3' end of the transcribed sequence;
   culturing said plant cells in a culturing medium containing a selection agent to identify plant cells containing said chimeric gene; and
   regenerating said plant cells containing said chimeric gene into whole plants.

17. A method of claim 16 wherein said plant is a species of plant from the Graminae family.

18. A method of claim 17 wherein said plant is rice.

19. A method of claim 16 wherein said structural DNA sequence is capable of conferring a selected agronomic trait to said plant.

20. A method for expressing a foreign structural gene in a plant under the regulatory control of a genome-length transcript promoter from rice tungro bacilliform virus comprising:
   transforming plant cells of said plant with a transformation vector comprised of a foreign structural gene under the regulatory control of a genome-length transcript promoter from rice tungro bacilliform virus; and
   growing said plant cells under conditions whereby said foreign structural gene is expressed under the regulatory control of said genome-length transcript promoter from rice tungro bacilliform virus.

21. A method for causing the expression of a structural DNA coding sequence in the vascular bundles of a plant, the method comprising;
   placing said structural DNA coding sequence under the regulatory control of a genome-length transcript promotor from rice tungro bacilliform virus, said structural DNA coding sequence being heterologous with respect to said promoter.

22. The method of claim 21 wherein said promoter has the nucleotide sequence of SEQ ID NO: 3.

23. The method of claim 21 wherein said promoter has the nucleotide sequence of SEQ ID NO: 5.

24. A DNA sequence consisting essentially of an isolated genome-length transcript promoter from rice tungro bacilliform virus.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

AGAAGATCTT CTACAA                  1 6

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

AGATCTGGTG CTCCTTAT                1 8

( 2 ) INFORMATION FOR SEQ ID NO:3:

( i ) SEQUENCE CHARACTERISTICS:
        ( A ) LENGTH: 714 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:3:

| AGATCTTCTA | CAAAAGGGAG | TAGTAATATT | TAATGAGCTT | GAAGGAGGAT | ATCAACTCTC | 60 |
|---|---|---|---|---|---|---|
| TCCAAGGTTT | ATTGGAGACC | TTTATGCTCA | TGGTTTTATT | AAACAAATAA | ACTTCACAAC | 120 |
| CAAGGTTCCT | GAAGGGCTAC | CGCCAATCAT | AGCGGAAAAA | CTTCAAGACT | ATAAGTTCCC | 180 |
| TGGATCAAAT | ACCGTCTTAA | TAGAACGAGA | GATTCCTCGC | TGGAACTTCA | ATGAAATGAA | 240 |
| AAGAGAAACA | CAGATGAGGA | CCAACTTATA | TATCTTCAAG | AATTATCGCT | GTTTCTATGG | 300 |
| CTATTCACCA | TTAAGGCCAT | ACGAACCTAT | AACTCCTGAA | GAATTTGGGT | TTGATTACTA | 360 |
| CAGTTGGGAA | AATATGGTTG | ATGAAGACGA | AGGAGAAGTT | GTATACATCT | CCAAGTATAC | 420 |
| TAAGATTATC | AAAGTCACTA | AAGAGCATGC | ATGGGCTTGG | CCAGAACATG | ATGGAGACAC | 480 |
| AATGTCCTGC | ACCACATCAA | TAGAAGATGA | ATGGATCCAT | CGTATGGACA | ATGCTTAAAG | 540 |
| AAGCTTTATC | AAAAGCAACT | TTAAGTACGA | ATCAATAAAG | AAGGACCAGA | AGATATAAAG | 600 |
| CTGGAACATC | TTCACATGCT | ACCACATGGC | TAGCATCTTT | ACTTTAGCAT | CTCTATTATT | 660 |
| GTAAGAGTGT | ATAATGACCA | GTGTGCCCCT | GGACTCCAGT | ATATAAGGAG | CACC | 714 |

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (i i) MOLECULE TYPE: DNA (synthetic)

(x i) SEQUENCE DESCRIPTION: SEQ ID NO:4:

| AGATCTTGCT | CTCTTAGAAG | TTT | | | | 23 |
|---|---|---|---|---|---|---|

(2) INFORMATION FOR SEQ ID NO:5:

(i) SEQUENCE CHARACTERISTICS:
      (A) LENGTH: 773 base pairs
      (B) TYPE: nucleic acid
      (C) STRANDEDNESS: single
      (D) TOPOLOGY: linear (i i) MOLECULE TYPE: DNA (genomic)

(x i) SEQUENCE DESCRIPTION: SEQ ID NO:5:

| AGATCTTCTA | CAAAAGGGAG | TAGTAATATT | TAATGAGCTT | GAAGGAGGAT | ATCAACTCTC | 60 |
|---|---|---|---|---|---|---|
| TCCAAGGTTT | ATTGGAGACC | TTTATGCTCA | TGGTTTTATT | AAACAAATAA | ACTTCACAAC | 120 |
| CAAGGTTCCT | GAAGGGCTAC | CGCCAATCAT | AGCGGAAAAA | CTTCAAGACT | ATAAGTTCCC | 180 |
| TGGATCAAAT | ACCGTCTTAA | TAGAACGAGA | GATTCCTCGC | TGGAACTTCA | ATGAAATGAA | 240 |
| AAGAGAAACA | CAGATGAGGA | CCAACTTATA | TATCTTCAAG | AATTATCGCT | GTTTCTATGG | 300 |
| CTATTCACCA | TTAAGGCCAT | ACGAACCTAT | AACTCCTGAA | GAATTTGGGT | TTGATTACTA | 360 |
| CAGTTGGGAA | AATATGGTTG | ATGAAGACGA | AGGAGAAGTT | GTATACATCT | CCAAGTATAC | 420 |
| TAAGATTATC | AAAGTCACTA | AAGAGCATGC | ATGGGCTTGG | CCAGAACATG | ATGGAGACAC | 480 |
| AATGTCCTGC | ACCACATCAA | TAGAAGATGA | ATGGATCCAT | CGTATGGACA | ATGCTTAAAG | 540 |
| AAGCTTTATC | AAAAGCAACT | TTAAGTACGA | ATCAATAAAG | AAGGACCAGA | AGATATAAAG | 600 |
| CTGGAACATC | TTCACATGCT | ACCACATGGC | TAGCATCTTT | ACTTTAGCAT | CTCTATTATT | 660 |
| GTAAGAGTGT | ATAATGACCA | GTGTGCCCCT | GGACTCCAGT | ATATAAGGAG | CACCAGAGTA | 720 |

```
GTGTAATAGA  TCATCGATCA  AGCAAGCGAG  AGCTCAAACT  TCTAAGAGAG  CAA                773
```